United States Patent
Shah et al.

(10) Patent No.: US 6,509,094 B1
(45) Date of Patent: Jan. 21, 2003

(54) POLYIMIDE COATED SHAPE-MEMORY MATERIAL AND METHOD OF MAKING SAME

(76) Inventors: Tilak M. Shah, 104 Lockberry La., Cary, NC (US) 27511; Richard E. Gordon, 70 Great Hill Rd., Ridgefield, CT (US) 06877

( * ) Notice: Subject to any disclaimer, the term of this patent is extended or adjusted under 35 U.S.C. 154(b) by 92 days.

(21) Appl. No.: 09/709,029

(22) Filed: Nov. 8, 2000

(51) Int. Cl.[7] .................................................. D02G 3/00
(52) U.S. Cl. ........................ 428/395; 428/364; 428/375; 428/378; 528/335; 528/353; 427/372.2; 427/384; 427/385.5; 427/388.1; 427/388.2; 427/393.5
(58) Field of Search ................................ 528/335, 353; 428/357, 364, 373, 375, 378, 395; 427/331, 372.2, 383.1, 384, 385.5, 388.1, 388.2, 393.5

(56) References Cited

U.S. PATENT DOCUMENTS

| | | | |
|---|---|---|---|
| 3,753,700 A | | 8/1973 | Harrison et al. |
| 5,092,781 A | | 3/1992 | Casciotti et al. |
| 5,120,308 A | * | 6/1992 | Hess ........................... 600/434 |
| 5,147,370 A | | 9/1992 | McNamara et al. |
| 5,226,979 A | * | 7/1993 | Thoma ........................ 148/402 |
| 5,911,731 A | | 6/1999 | Pham et al. |
| 5,964,744 A | | 10/1999 | Balbierz et al. |
| 6,080,160 A | | 6/2000 | Chen et al. |
| 6,099,563 A | | 8/2000 | Zhong |
| 6,162,893 A | * | 12/2000 | Choi et al. ................... 528/353 |

FOREIGN PATENT DOCUMENTS

JP          405051759 A   *  3/1993   ........... C23C/18/38

* cited by examiner

*Primary Examiner*—James J. Seidleck
*Assistant Examiner*—Travis B Ribar
(74) *Attorney, Agent, or Firm*—Marianne Fuierer; Steven J. Hultquist; Yongzhi Yang

(57) ABSTRACT

Disclosed is a polyimide coated shape memory material suitable for thermomechanical treatment to shape-set the material into the desired configuration and activate shape memory properties. The polyimide coating is subjected to a curing regime that imparts higher heat resistance in the polyimide coating to withstand the elevated temperatures required during the shape-setting treatment.

15 Claims, 2 Drawing Sheets

POLYIMIDE COATED SHAPE-MEMORY MATERIAL AND METHOD OF MAKING SAME

BACKGROUND OF THE INVENTION

1. Field of the Invention

The present invention relates to polymeric coatings on shape memory materials. More specifically, it relates to polyimide coatings on shape memory alloys that are capable of withstanding elevated temperatures required to effectively form shape memory materials into a desired configuration.

2. Description of the Related Art

Shape memory materials, such as shape memory alloys, include materials having anthropomorphic qualities of memory and trainability. A particularly useful attribute of these alloys is that when they are plastically deformed at a particular temperature, they can completely recover their previous shape by superelastic or shape memory mechanisms after receiving the appropriate thermal mechanical conditioning procedure. The defined shape or size can be achieved through thermomechanically shapesetting the materials. For example, the shape memory material is typically processed by being restrained in the desired memory shape while increasing the temperature within the material to set this shape.

The ability to revert to a previously defined shape or size has broad applicability in many different fields. For example, the medical industry has incorporated shape memory materials into a number of products including catheter guidewires, stents, surgical hooks, vasoocclusive devices, suturing and stapling devices. Many other consumer and industrial products have been fabricated from the shape memory materials, including eyeglass frames, cellular telephone antennas, damping devices, orthodontic arches, brassiere underwires and the like.

In many of the above-identified applications, it is desirable or necessary to apply a polymeric coating to the surface of a component fabricated from shape memory material. For instance, a coating may be required to extend the component's useful life, act as an adhering surface for bonding additional polymeric features, act as an insulator, enhance biocompatibility of the component and the like.

Heretofore, if a polymeric coating was required on a component made of shape memory material, the coating was applied after thermomechanical heat treatment to shape-set the material because the polymeric materials utilized for coating were incapable of withstanding the elevated temperatures required for subsequent thermomechanical shapesetting the material. However, applying a polymeric coating, after the shape-setting process, is labor-intensive, requiring multiple steps and additional time. Furthermore, a number of quality control factors are presented that impact the final product, such as lack of uniformity in the coating thickness and inability to apply very thin films to the surface.

Heretofore, coatings have been applied by processes that involved several steps. For example, U.S. Pat. No. 5,443,907 discloses a method for coating medical insertion guides. The method described by the '907 patent includes installing a polyurethane sleeve on a core wire, which may be a pre-shaped and heated nitinol wire, and heating the polymeric sleeve to a temperature until it is reformed around the core. However, such a method, entailing several manual steps, increases the cost of production and decreases efficiency.

Accordingly, there is a need for improved polymeric-coated shape memory materials and methods of making same that provide precoated shape memory elements that withstand the elevated temperatures required during shape-setting treatment, have coatings with essentially uniform thickness, have very thin coatings if desired, and minimize time and effort required for the coating process thereby increasing efficiency and decreasing cost.

SUMMARY OF THE INVENTION

As used herein, the terms and expressions below, appearing in the specification and claims, are intended to have the following meanings:

"Shape memory properties" as used herein includes thermal shape memory effects characterized by the ability of a material to recover a pre-set shape upon heating; and mechanical superelasticity effects characterized by the ability to withstand high elastic strain and recover the initial shape after release of the strain.

"Thermomechanical treatment" as used herein in reference to treatment of a shape memory material means a heat treating regime to shape-set the shape memory material where the material may or may not be restrained during the treatment.

A principal object of the present invention is to provide a shape memory material coated with a polymeric coating wherein the polymeric coating is applied before thermomechanical treatment of the shape memory material to activate the shape memory properties and shape-set into the desired configuration.

Another object of the present invention is to provide a polyimide coating that withstands higher temperatures required to shape-set the shape memory material.

A further object of the present invention is to provide an improved method of coating shape memory material to decrease overall production costs and increase efficiency.

A still further object of the present invention is to provide a method for increasing adhesion of polymeric materials to shape memory materials thereby overcoming problems associated with non-adhering polymer extensions.

Another object of the present invention is to provide essentially uniform coatings on surfaces fabricated from shape memory material.

Yet another object of this invention is to provide a coated shape memory material that exhibits reduced temperature variations in the shape memory material when the shape memory element is heated electrically by $I^2R$ and held in contact with shaping guides and fixtures which act as a heat sink.

Still another object of this invention is to provide electrically and thermally activated devices fabricated from the disclosed polyimide coated shape memory material having electrical insulating abilities for high dielectric isolation from other components in the systems.

These and further objectives are accomplished by the materials and methods disclosed herein.

In one aspect, the present invention relates to a shape memory material coated with at least one cured polymeric material that is capable of withstanding the elevated temperatures normally required to effectively thermomechanically shape-set the shape memory material into a desired configuration. Advantageously, the polymeric material may be cured previously to or concurrently with the thermomechanical shape-setting process.

Generally, any polymeric material, that in the cured stated exhibits heat resistant properties to withstand the elevated temperatures of the shape-setting process, may be employed.

Illustrative polymeric materials having utility in various applications of the invention include, without limitation polyimides, polybenzimidazoles, polybenzoxazoles, polybenzothiazoles, polyoxadiazoles, polytiazoles, polyquinoxalines, polyimidazopyrrolones, and bismaleimide, polyamideimide, and compatible mixtures, blends and copolymers (of monomers) thereof.

In one preferred embodiment of the present invention, a cured polyimide coated element of a shape memory alloy is provided by coating an element of the shape memory alloy, which has not been thermomechanically heated to exhibit shape memory properties, with a polyimide material on at least a portion of the element of the shape memory alloy. The polyimide coating may be cured and then subjected to a thermomechanical heating regime necessary to exhibit shape memory properties. In the alternative, the curing of the polyimide coating may be simultaneously achieved during the thermomechanical heating regime. The polyimide coating is heat cured at a sufficient temperature to withstand the elevated temperatures of the subsequent or concurrent thermomechanically heating regimes required to shape-set the desired configuration.

Serendipitously and unexpectedly, it has been found that if the polyimide coating is heat cured within a certain elevated temperature range, the softening temperature and melting temperature of the polyimide is driven higher thereby allowing the polyimide coating to withstands higher temperatures. As a result, the polyimide coating is able to maintain its stability by retaining polymeric properties and behavior during the shape-setting heat treatment and after. Generally, the heat curing temperature range is from about 200° C. to about 400° C., preferably from about 250° C. to about 350° C., and more preferably from about 300° C. to about 350° C. Curing time may be dependent on the thickness of the coating which is predetermined by the specific application of the component. Generally for a thin film of from about 1 to about 2 mils, the curing time will range from about 1 minute to about 5 minutes.

The cured polyimide coated shape memory elements preferably are characterized by having essentially uniform coatings, at a desired thickness, on all coated surfaces to provide advantages including uniform heating through the entire element of component during the thermomechanical heating regime for shape-setting.

Other objects, features and embodiments of the present invention will be more fully apparent from the ensuing disclosure and appended claims.

DETAILED DESCRIPTION OF THE INVENTION AND PREFERRED EMBODIMENTS THEREOF

In accordance with the present invention, there is provided polymeric coated shape memory materials wherein the polymeric coating retains its stability and integrity through the elevated heating regime required to train the shape memory material into a desired configuration.

Figure 1:
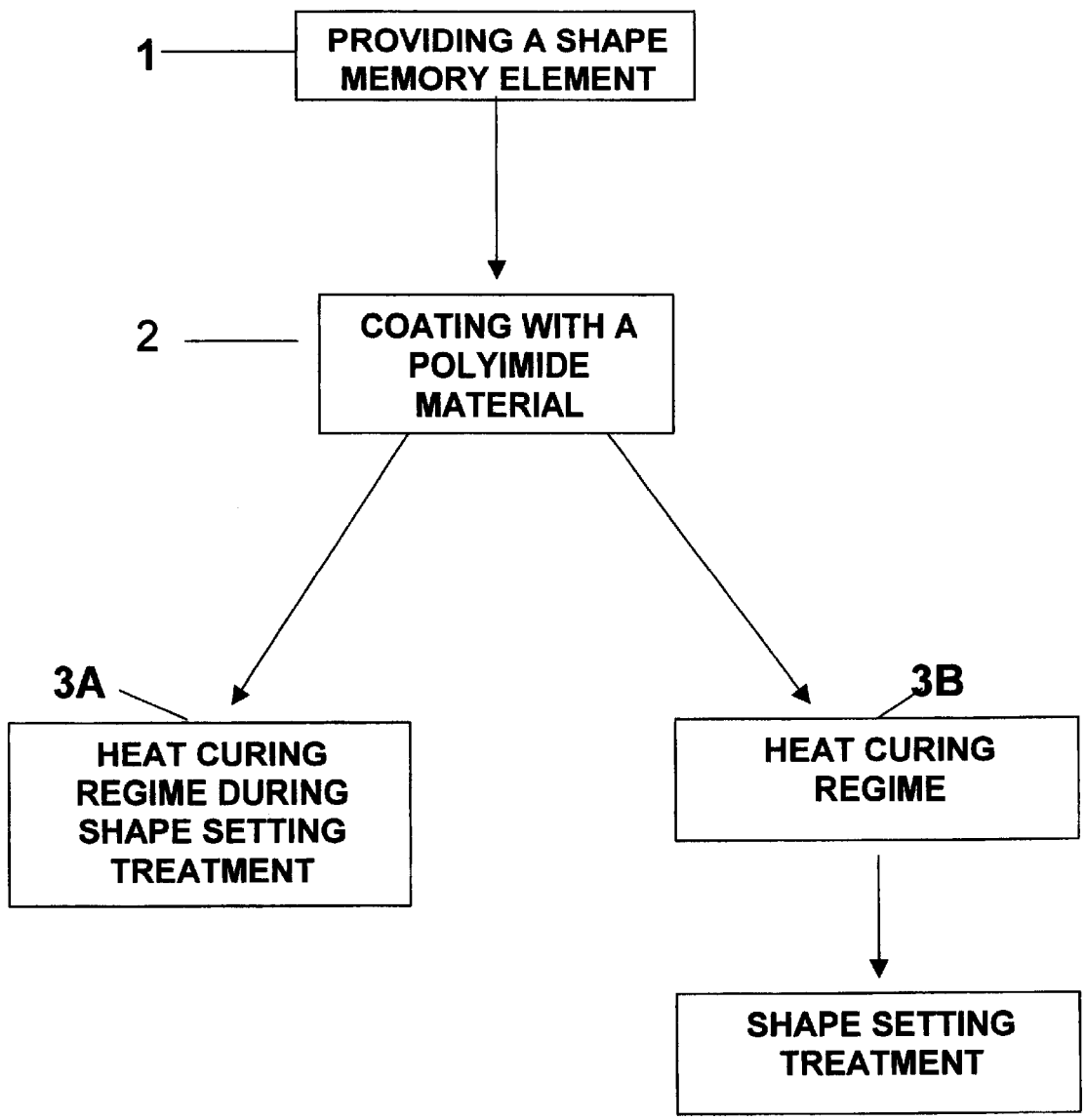
FIG. 1 depicts a process flow for coating and heat treating a shape memory element.
Figure 2:
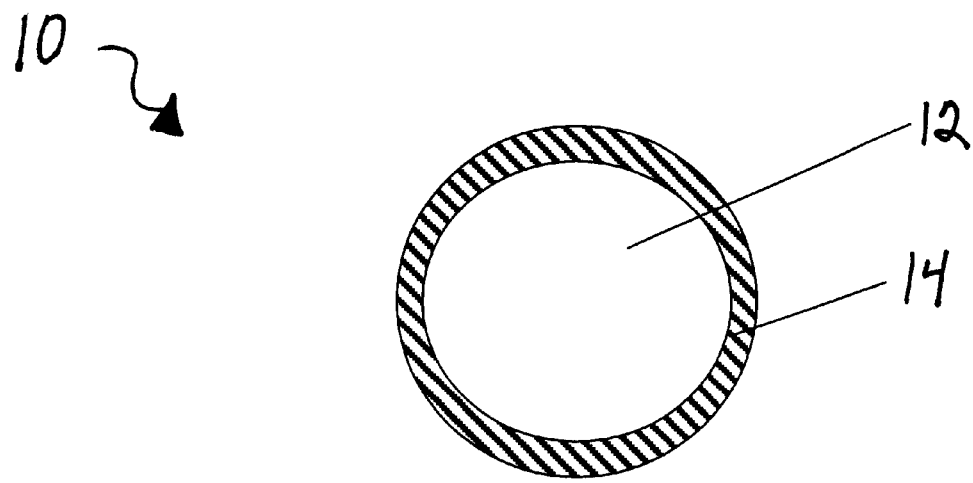
FIG. 2 illustrates a cross-sectional view of a wire component having coated thereon a surface polyimide coating.

Methods of the present invention can be demonstrated by reference to FIG. 1 which shows a process flow diagram for the steps of coating and training the shape memory material to provide the coated shape memory materials shown in FIG. 2.

Shape memory materials, such as shape memory alloys are defined as materials that have the ability to remember a trained shape even after deformation. The trained shape is set by thermomechanical training wherein the component of the shape memory alloy is heated to a temperature typically ranging from about 300° C. to about 800° C. with the components usually being restrained in the desired shape. Shape memory alloys undergo a phase-transformation in the crystal structure when cooled from the stronger higher temperature crystal structure (austenite) to the weaker lower temperature crystal structure (martensite). As a result, when the shape memory alloy is in the weaker martensite crystal structure it can be easily deformed to a new shape, but when heated to above its transformation temperature, that being when the martensite crystal structure is converted to the austenite crystal structure, the shape memory alloy reverts to its previous stronger crystal structure and shape. This is known as the shape recovery effect.

Shape memory alloy undergo a phase transformation at constant temperature, when the stronger higher temperature structure (austenite) is mechanically deformed thereby stress inducing a change in crystal structure to martensite. This is known as superelasticity.

For purposes of the present invention, any shape memory material that exhibits shape memory properties and has a transformation temperature ranging from about −270° C. to about 100° C. may be used in the present invention. Specifically, shape memory alloys found to be particularly effective include, without limitation at least one member selected from the group of AgCd; AuCd; NiTi; NiAl; NiTiX where X is Cu, Fe, Nb, Hf, Pd, Au, Ag, and Pt; CuAlNi; CuSn; CuZn; CuZnX where X is Si, Sn, Al; InTi; FePt; MnCu; and FeMnSi.

Very desirable materials, from a mechanical point of view, are "superelastic alloys" including NiTi alloys, and NiTiX alloys. Especially preferred are the NiTi alloys known as "nitinol". These are sturdy alloys which will tolerate significant flexing without deformation even when used to form very small diameter wire.

The shape memory alloys may be heated and the melted ingots forged, extruded, bar rolled and the like into shape memory elements such as wires, strips, tubing and the like. Most cold working processes may also be used with these alloys. Wire drawing is a widely used technique to provide thin wires that subsequent to shape-setting by thermomechanical means may be used in a multitude of applications, such as orthodontic archwire, guidewires, stents, needles, springs, bra underwires, antenna wires, eyeglass frames and the like.

It may be advantageous to cut the shape memory material elements into the desired lengths and/or sizes before the coating process of the present invention to reduce productions costs and provide a coating on all surfaces, including end surfaces, if desired. In the alternative, the cold worked shape memory material element may be continuously coated and heat treated to cure the polymeric coating.

In one aspect of the present invention, an element of a shape memory material, that has not been subjected to the shape-setting treatment, is coated with a polymeric material that upon curing is able to withstand high temperatures required to shape-set the shape memory material into a desired configuration while retaining its polymeric physical properties such as strength, thermal temperature resistance and stress-strain mechanical behavior.

As stated above, any polymeric material that upon curing possesses the heat resistant properties to withstand the elevated temperatures of the shape-setting process may be applied. More specifically, illustrative polymeric materials include polyimides, polyetherimides, polybenzimidazoles, polybenzoxazoles, polybenzothiazoles, polyoxadiazoles, polytiazoles, polyquinoxalines, polyimidazopyrrolones, bismaleimide, polyamideimide and compatible mixtures, blends and copolymers (of monomers) thereof.

Polyimides are an especially preferred polymeric material and characterized by the presence of the phthalimide structure in the polymer backbone as shown below:

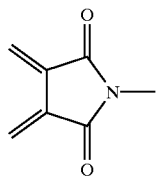

and may include, for example, polymers based on condensation reactions of an oxydianiline and a pyromellitic dianhydride, polyaminobismaleimide, and mixtures thereof, all of which have imide linkages, high molecular weight, and after curing as described herein, have increased thermal resistance and are able to withstand the elevated temperatures required for shape-setting the shape memory substrate. More preferred polyimides include prepolymers of oxydianiline and pyromellitic dianhydride which cure to form polyimides after coated on a wire.

As stated above, polyimides are a group of polymers generally formed by the condensation of an organic anhydride or dianhydride with a diamine. Generally, they are synthesized by a two-stage process. The first stage involves an amidation reaction to produce a high molecular weight poly(amic acid). The poly(amic acid) is formed into the desired physical form of the final polymer product, e.g., film, fiber, laminate, coating, etc. and then the second stage of the reaction is carried out. The poly(amic acid) is cyclized in the solid-state to the polyimide by heating at a moderately high temperature above 150° C.

The polyimide surface coating may be applied to at least a portion of the surface of the shape memory material by a variety of processes that are well known in the art. For example, surface coating may be accomplished by dipping, spraying, extruding, extrusion coating, laminating, insert molding the coating onto the surface, and the like. Preferably, the chosen method provides an essentially uniform coating in the desired areas of coverage. The areas of coverage on the surface may be continuous or patterned dependent on the final use and application of the element fabricated from a shape memory material. Moreover, a surface coating may be applied to an internal surface and/or an external surface. For example, in the case of a tubing element fabricated from shape memory material, both the external and internal surfaces of the tube may be coated.

The thickness of the polyimide coating deposited on the shape memory substrate is determinant on the specific end product and its particular application. For instance, if the coating is merely a bonding surface to ensure adhesion of another polymeric material, then the film layer may be sufficiently thin. In contrast, the coating may be for the general purpose of providing a comfort coating for an underwire bra support wire or an insulating barrier between electronic components, and as such, requires a thicker layer. Generally, the coating may have an average thickness of about 0.5 mils to 5 mils, and more preferably, from about 1 to about 2 mils.

To effect proper adhesion of the polyimide coating to the surface of the shape memory material, cleaning and/or pretreating of the surface may be necessary and any of various effective procedures known to those skilled in the art may be utilized.

After the polyimide coating (which may be a first stage poly(amic acid)) has been applied to the shape memory element, the coating must be heat cured to ensure that the polymeric coating has effective heat resistant properties to withstand the elevated temperatures required in the thermomechanical shape-setting treatment. The heat curing process may be performed before the thermomechanical shape-setting treatment, or in the alternative, during the shape-setting treatment wherein the elevated temperatures not only shape the material into the desired configuration and activate the shape memory properties but also cure the polyimide coating.

If the polyimide coated shape memory material is heat cured before the shape-setting treatment, a simple heating chamber may be used. In one embodiment, the heat curing regime for proper curing of the polymer, to impart the higher heat resistance properties, includes the steps of slowly elevating the temperature within the material to a temperature ranging from about 250° C. to about 500° C. and then as a final step, raising the temperature sharply to a much higher temperature ranging from about 400° C. to 600° C. for a limited duration of about 1 second to about 5 seconds. Advantageously, this final rise to a higher than normal curing temperature imparts a higher heat resistance temperature in the polymer, thereby providing additional strength in the material and stability to withstand even higher temperatures and/or the mechanical manipulation required to shape-set the material.

In the alternative, the polyimide coated shape memory material may be heat cured during the thermomechanical shape-setting treatment. This can be accomplished in a number of ways, for example, placing the coated element in an oven and initiating the heat curing regime as defined above. The early stage of the shape-setting treatment occurs concurrently and by the time the final high temperatures are reached for shape-setting, the polyimide coating has been sufficiently heat cured to withstand these higher temperatures. In the alternative, the coated shape memory material may be heat cured by resistant heating which involves passing a current along or through the material to elevate its temperature. During the thermomechanical shape-setting treatment, the shape memory material may need restraining in the desired shape, otherwise it may not remain in such shape. The appropriate temperature to "shape-set" the material may range from about 200° C. to about 800° C., depending on the material and time allowed for the heat treatment.

Heretofore, when resistant heating, commonly referred to as $I^2R$ heating, was used to shape-set shape memory material, there were a number of inherent problems including temperature variations throughout the material which lead to non-homogenous mechanical properties in the final product. Temperature variations can be caused by non-uniform contact of the shape memory material with the forming tool and/or by the forming tool acting as a heat sink and drawing heat from the material. Advantageously, the polyimide coated material of the present invention promotes more uniform heating of the shape memory material, and thus, minimizes the negative effects of local heat sinks. Also, the intact polyimide act as an insulator for heat and minimize heat loss.

Figure 3:
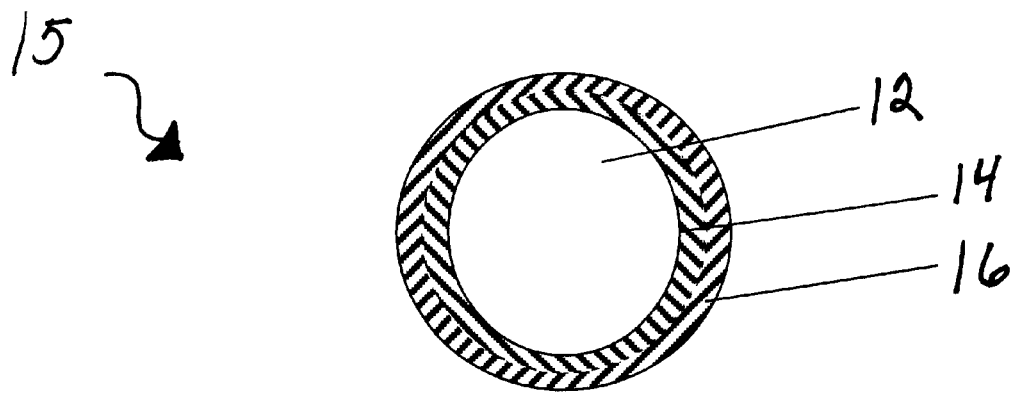
FIG. 3 illustrates a cross-sectional view of a polyimide coated wire component having a second polymeric coating thereon.

After completion of the shape-setting treatment, the polyimide coated shaped component provides an excellent bonding surface for adhesion of additional polymeric extensions or polymeric coatings, as for example is shown in FIG. 3. For instance, blunt ends of underwire bra supports, coated by the present method, can be augmented with polymeric extensions to provide increased comfort for the wearer. Likewise, coated wires used for eyeglass frames may have an additional polymeric coating thereon to impart fashion related colors.

Generally any polymeric material that adheres to the polyimide surface may be applied as a second or additional coating, for example, olefin polymers, polyesters, polyurethanes, silicone rubbers, polyamides, polyadehydes, natural rubbers, polyether-ester copolymers and polyether-amide copolymers, polyacrylate, polycarbonate and the like.

The present invention contemplates the use of polyimide coated shape memory elements, prepared according to the methods of the present invention, in conjunction with medical devices, cellular phone antennas, means to create a mechanical joint. The coating surface may be modified by bonding additional polymers to the base substrate which can in turn be joined to other components in a larger system.

Although the invention has been disclosed herein with reference to various embodiments and features, it will be appreciated that the embodiments and features described hereinabove are not intended to limit the invention, and that other variations, modifications, and other embodiments will suggest themselves to one of ordinary skill in the art. The invention therefore is to be broadly construed, consistent with the claims hereafter set forth.

That which is claimed is:

1. A process for making a cured polyimide coated element having shape memory properties comprising the following steps:
   a) providing an element of a shape memory alloy which has not been thermomechanically heated to exhibit shape memory properties;
   b) applying a polyimide coating on at least a portion of the element of the shape memory alloy; and
   c) curing the polyimide coating at a sufficient temperature to withstand the elevated temperatures of shape-setting treatment to provide a cured polyimide coated element of the shape memory alloy for shaping into the desired configuration by thermomechanically heating to exhibit shape memory properties.

2. The process according to claim 1 wherein the curing of the polyimide coating is accomplished before thermomechanically heating to exhibit shape memory properties.

3. The process according to claim 1 wherein the curing of the polyimide coating is accomplished during thermomechanically heating to exhibit shape memory properties.

4. The process according to claim 1 further comprising applying a second polymeric coat to the cured polyimide coated element.

5. The process according to claim 1 wherein the polyimide coating is cured at a temperature ranging from about 250° C. to about 400° C.

6. A cured polyimide coated element of a shape memory alloy suitable for heating to a desired configuration comprising:
   a) an element of the shape memory alloy which has not been thermomechanically heated to exhibit shape memory properties;
   b) a polyimide coating positioned on at least a portion of the element of the shape memory alloy that is exposed to a sufficient temperature to heat cure the polyimide coating and impart heat resistance to withstand the elevated temperatures of a shape-setting treatment thereby providing the cured polyimide coated element of the shape memory alloy.

7. A cured polyimide coated element of a shape memory alloy according to claim 6 wherein the shape memory alloy is at least one member selected from the group consisting of AgCd, AuCd, CuAlNi, CuSn, CuZn, CuZnSi, CuZnSn, CuZnAl, InTi, NiAl, NiTi, NiTiCu, NiTiFe, NiTiNb, NiTiHf, NiTiPd, NiTiAu, NiTiAs, NiTiPt, FePt, MnCu, and FeMnSi.

8. A cured polyimide coated element of a shape memory alloy according to claim 6 wherein the polyimide coating is of sufficient thickness to impart insulating properties to the shape memory alloy.

9. The process according to claim 1, wherein the shape memory alloy is at least one member selected from the group consisting of AgCd, AuCd, CuAlNi, CuSn, CuZn, CuZnSi, CuZnSn, CuZnAl, InTi, NiAl, NiTi, NiTiCu, NiTiFe, NiTiNb, NiTiHf, NiTiPd, NiTiAu, NiTiAs, NiTiPt, FePt, MnCu, and FeMnSi.

10. The process according to claim 1, wherein the polyimide coating is of sufficient thickness to impart insulating properties to the shape memory alloy.

11. The cured polyimide coated element of a shape memory alloy according to claim 6 further comprising a second polymeric layer bonded thereon.

12. The cured polyimide coated element of a shape memory alloy according to claim 6 wherein the sufficient temperature for curing the polyimide coating ranges from about 250° C. to about 400° C.

13. The cured polyimide coated element of a shape memory alloy according to claim 6 wherein the polyimide coating is characterized by having a uniform thickness.

14. A process for making a cured polymeric coated element having shape memory properties comprising the following steps:
   a) providing an element of a shape memory alloy which has not been thermomechanically heated to exhibit shape memory properties;
   b) applying a polymeric coating on at least a portion of the element of the shape memory alloy; and
   c) curing the polymeric coating at a sufficient temperature to withstand the elevated temperatures of shape-setting treatment to provide a cured polymeric coated element of the shape memory alloy for shaping into the desired configuration by thermomechanically heating to exhibit shape memory properties.

15. A cured polymeric coated element of a shape memory alloy suitable for heating to a desired configuration comprising:
   a) an element of the shape memory alloy which has not been thermomechanically heated to exhibit shape memory properties;
   b) a polymeric coating positioned on at least a portion of the element of the shape memory alloy that is exposed to a sufficient temperature to heat cure the polymeric coating and impart heat resistance to withstand the elevated temperatures of a shape-setting treatment thereby providing the cured polymeric coated element of the shape memory alloy.

* * * * *